United States Patent
Mukherjee

(10) Patent No.: US 6,310,188 B1
(45) Date of Patent: Oct. 30, 2001

(54) METHOD FOR PRODUCING CHITIN OR CHITOSAN

(75) Inventor: Debi P. Mukherjee, Shreveport, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/490,763

(22) Filed: Jan. 24, 2000

(51) Int. Cl.⁷ .................................................. C08B 37/08
(52) U.S. Cl. ............................................ 536/20; 536/127
(58) Field of Search ........................................ 536/20, 127

(56) References Cited

U.S. PATENT DOCUMENTS

| | | | |
|---|---|---|---|
| 3,862,122 | 1/1975 | Peniston et al. | 260/211 R |
| 4,066,735 | 1/1978 | Peniston et al. | 423/159 |
| 4,195,175 | 3/1980 | Peniston et al. | 536/20 |

OTHER PUBLICATIONS

No, H. et al., "Preparation of chitin and chitosan," pp. 475–489 in R. Muzzarelli et al. (Eds.), *Chitin Handbook* (1997).
Caplus abstract of Signini, R. et al "Purification and characterization of commercial chitosan" Polim.: Cienc. Tecnol. vol. 8 No. 4 pp. 63–68, 1998.*

Bienvenu, J., "Development of a Process to Produce Chitosan from Crawfish Waste," report presented at Louisiana Region I Science and Engineering Fair, Bossier City, Louisiana (Mar. 18–19, 1999); and at the International Science and Engineering Fair, Philadelphia, Pennsylvania (May 1999).

* cited by examiner

*Primary Examiner*—James O. Wilson
*Assistant Examiner*—Leigh C. Maier
(74) *Attorney, Agent, or Firm*—John H. Runnels

(57) ABSTRACT

A method is disclosed for improving the efficiency of producing chitin and chitosan, particularly biocompatible chitosan. Crustacean shells are maintained at a high temperature for a sufficient time to convert most of the chitin in the shells to an amorphous form. The shells are then rapidly cooled, for example by plunging into liquid nitrogen, so that most of the chitin in the shells remains in the amorphous form. These "quenched" shells are then deproteinized and demineralized to produce chitin. The chitin may be deacetylated to produce chitosan. High purity chitin or chitosan is thereby produced at a lower cost than has been possible using previous methods. Biocompatible chitosan produced by this process may be used for the delivery of cells or bioactive agents, or for other applications. It is believed that the heating followed by immediate quenching enhances the formation of chitin chains in an amorphous or a relaxed form, making them more susceptible to attack by acid or alkali during the subsequent treatment steps. Making the chitin amorphous allows the more efficient and economical production of chitosan, using lower quantities of chemicals such as hydrochloric acid and sodium hydroxide, thus making the entire production process both more economical and less polluting.

12 Claims, No Drawings

METHOD FOR PRODUCING CHITIN OR CHITOSAN

This invention pertains to a method for producing chitin or chitosan, particularly to a method for producing chitin or chitosan from crustacean shells.

Chitosan is a biopolymer with many uses in the health care industry. To take just a few examples, chitosan may be used as a cell delivery vehicle, in a synthetic bone graft material (e.g., a mixture of chitosan and hydroxyapatite), in spinal fusions, and in various wound healing applications. Chitosan has also been marketed for use in consumer products that are said to reduce fat and cholesterol.

Chitosan and its precursor, chitin, are typically prepared from waste shells of crustaceans, particularly decapod crustaceans such as crab, shrimp, crawfish, krill, lobster, and prawn. The conventional process for producing chitin and chitosan from crustacean shells is described, for example, in H. No et al., "Preparation of chitin and chitosan, " pp. 475–489 in R. Muzzarelli et al. (Eds.), *Chitin Handbook* (1997). Crustacean shells are ground and treated with dilute sodium hydroxide and heat to remove protein (deproteinization). Calcium carbonate is removed by extraction with dilute hydrochloric acid at room temperature (demineralization). Following deproteinization and demineralization, the resulting product is predominantly chitin. An optional decolorization step may be used to bleach the chitin, for example, extraction with ethanol and ether, or bleaching with sodium hypochlorite. Removal of acetyl groups from the chitin polymer (deacetylation) produces chitosan; deacetylation is usually performed by reacting chitin with concentrated sodium hydroxide or potassium hydroxide and heat. Deacetylation need not be complete. No et al. observed that the characteristics of chitin and chitosan differ, depending on the crustacean species used for the starting material and the particular preparation method used.

Variations on the basic process for producing chitosan are disclosed, for example, in U.S. Pat. Nos. 3,862,122, 4,066,735, and 4,195,175.

Work done under the supervision of the present inventor was described in J. Bienvenu, "Development of a Process to Produce Chitosan from Crawfish Waste," report presented at Louisiana Region I Science and Engineering Fair, Bossier City, La. (March 18–19, 1999); and at the International Science and Engineering Fair, Philadelphia, Pa. (May 1999).

Prior methods of producing chitosan are expensive, especially methods of producing high-purity chitosan. There is an unfilled need for a less expensive method for producing chitosan, particularly a chitosan of high purity that is suitable for biomedical uses.

I have discovered a method for improving the efficiency of producing chitin and chitosan, particularly chitosan of high purity that is suitable for biomedical uses. Cleaned crustacean shells are maintained at a high temperature for a sufficient time to convert most of the chitin in the shells to an amorphous form. The shells are then rapidly cooled, for example by plunging into liquid nitrogen, so that most of the chitin in the shells remains in the amorphous form. These "quenched" shells are then deproteinized and demineralized to produce chitin. The chitin may be deacetylated to produce chitosan. High purity chitin or chitosan is thereby produced more efficiently and at a lower cost than has been possible using previous methods. An optional dialysis step to remove low molecular weight compounds can further improve the purity of the chitosan. The resulting chitosan is biocompatible and can be used for the delivery of cells or bioactive agents, or for other applications.

Without wishing to be bound by this theory, it is believed that the heating followed by immediate quenching enhances the formation of chitin chains in an amorphous or a relaxed form, making the chitin more susceptible to attack by acid or alkali during, the subsequent treatment steps. Making the chitin amorphous allows the more efficient and economical production of chitosan, using lower quantities of chemicals such as hydrochloric acid and sodium hydroxide, thus making the entire process both more economical and less polluting.

EXAMPLE 1

Preparation of Chitin

Cleaning the Crawfish Shells

About 50 g of waste crawfish shells (*Procambarus clarkii*) were collected and boiled in water for 1 hour to remove as much of the tissue from the shells as possible. The shells were then placed in a 163° C. oven for 1 hour. The shells were then removed from the oven, and any dried tissue remaining on the shells was scrubbed off. An optional pre-treatment of the shells (which was not used in this particular example) is to immerse the shells in a dilute bleach solution and wash them prior to the boiling step.

Quenching the Shells

The cleansed shells (about 20 g) were placed in an 80° C. oven for 48 hours to break down the crystalline structure of chitin in the shells. After 48 hours, the shells were removed from the oven and immediately dumped into a container holding 2.5 liters of liquid nitrogen, thereby quenching the shells. Rapidly cooling the shells is believed to prevent or inhibit the re-formation of crystalline chitin, making the chitin more amorphous. The shells were removed from the liquid nitrogen after obvious boiling had subsided, and the quenched shells were quickly ground into small flakes with a mortar and pestle. In addition to the quenching effect, the liquid nitrogen temperature also made the shells very brittle, making it easier to grind the shells into finer particles.

Although cooling in a liquid nitrogen bath is preferred, other methods for rapid cooling could also be used, for example rapid cooling in a liquid—dry ice bath, such as an acetone—dry ice bath or an ethanol—dry ice bath.

Deproteinization

About a day later, 1.0 g of the quenched shells were placed in 10 mL of 3.5% NaOH solution (1:10 ratio w/v) for 2 hours at a temperature of 65° C. After two hours, the supernatant was removed, and the shells were left to dry at 90° C. The mass of the residue left from the supernatant was recorded to determine the amount of protein removed from the shells. The shells were washed with nanopure water and dried at 90° C. The mass of the dried shells was 675.3 mg.

Demineralization

The deproteinized shells were placed in 10.15 mL of 1 N HCl (1:15 ratio w/v) at 25° C. for two hours. The supernatant was removed at the end of two hours, and the shells were allowed to dry. The mass of the residue left from the supernatant was recorded to determine the amount of mineral content removed from the shells. The shells were then washed with nanopure water and again dried. The mass of the dried shells was 404.6 mg. Following this treatment, the dried shells comprised primarily chitin.

EXAMPLE 2

Preparation of Chitosan

Deacetylation

The chitin from Example 1 was added to 10 mL of 50% NaOH (1:25 ratio w/v) and placed in an 80° C. oven for 96 hours. This treatment removed many of the acetyl groups from chitin to form chitosan. At the end of the 96 hours, the supernatant was removed from the depleted shell material. Since chitosan is soluble in both acids and bases, the chitosan was now dissolved in the supernatant. Titrating to pH 7.0 with 7 N HCl caused the chitosan to precipitate out. The precipitate was centrifuged, and the pellet of chitosan was separated from the supernatant. The precipitate was left to dry, and its mass was then found to be 333.8 mg.

EXAMPLE 3

Purification of Chitosan

The dried precipitate was ground into a powder and dissolved in a 2% acetic acid solution at a ratio of 1:100 (w/v). This solution was then placed into 12,000–14,000 Dalton Dialysis Tubing. The tubing was placed in a tray filled with the same concentration of acetic acid for 24 hours to remove low molecular weight compounds, i.e., those having a molecular weight below about 12,000 to 14,000. The solution inside the tubing was then removed and dried in vacuum. The mass of the purified chitosan was measured as 198.5 mg.

A 12,000–14,000 Dalton dialysis membrane was chosen simply because it was readily available. Dialysis membranes with other molecular weight cutoffs could also be used. The objective of the dialysis step is to remove low molecular weight proteins, calcium salts, and low molecular weight degradation products of chitin or chitosan. This purification step should increase the biocompatibility of the chitosan.

Characterization of the product by HPLC showed a single peak, indicating a pure product. That peak was almost identical to the peak resulting from an HPLC analysis of a commercially-obtained, high quality grade of chitosan—indicating that both had comparable levels of purity, and similar molecular weights.

EXAMPLES 4 and 5

Ten gram Preparation of Chitin and Chitosan

The procedures of Examples 1–3 above (deproteinization through purification) were repeated using 10 g of quenched shells at the beginning of the deproteinization step (rather than 1 g), and adjusting ratios of all other reactants and solutions proportionately. The results are shown in Table 1.

TABLE 1

| Initial Quenched Shell Mass | % of Initial Mass After Deproteinization | % of Initial Mass After Demineralization | % of Initial Mass After Deacetylation | % of Initial Mass After Dialysis |
| --- | --- | --- | --- | --- |
| 1 g | 67.53 | 40.46 | 33.38 | 19.85 |
| 10 g | 69.58 | 33.55 | 29.78 | 15.08 |

EXAMPLES 7 and 8

Comparison of the Process with and without Quenching

These two examples compared chitosan produced by the process just described, versus that produced by an otherwise identical process omitting the initial heating step followed by immediate quenching. The crawfish shells used as the raw material in these two examples were from the same batch.

EXAMPLE 7

Step 1. Heating, Quenching, Grinding. Shells were placed in an 80° C. oven for 48 hours, followed by immediate quenching in liquid nitrogen and grinding.

Step 2. Deproteinization. 2.1 g of quenched shells were immersed in ten mL of 3.5% NaOH for 2 hours at 65° C. After 2 hours, the shells were removed, washed with nanopure water, and dried.

Step 3. Demineralization. Dried shells were immersed for 2 hours in a 1 N HCl solution having a volume (in mL) equal to ten times the mass of the shells (in g). The shells were then washed with nanopure water and dried.

Step 4. Deacetylation. Dried shells were immersed in a 50% NaOH solution having a volume (in mL) equal to ten times the mass of the shells (in g), and were heated in an 80° C. oven for 96 hours. The supernatant was separated and filtered though a 0.2-micron filter. The pH was lowered to 7.0 by titration with 7 N HCl to precipitate out the chitosan. The solution was centrifuged at 2000 r.p.m. for 5 minutes. The precipitate was dried overnight.

Step 5. Purification. The dried chitosan product was purified by dissolving it in 50% NaOH, followed by neutralization to pH 7.0 with HCl to precipitate out the purified chitosan. The solution was centrifuged to collect the purified chitosan, which was then dried overnight in an oven.

Step 6. Dissolution. The dried powder was immersed in a 2% acetic acid solution to make a 0.1% chitosan solution. The powder dissolved in 2% acetic acid solution, demonstrating that the chitosan was of high purity.

EXAMPLE 8

Step 1. Quenching, Grinding. Shells without the immediately preceding heat treatment were placed in liquid nitrogen and then ground.

Step 2. Deproteinization. Same as in Example 7.

Step 3. Demineralization. Same as in Example 7.

Step 4. Deacetylation. Same as in Example 7.

Step 5. Purification. Same as in Example 7.

Step 6. Dissolution. The dried powder was immersed in a 2% acetic acid solution to attempt to make a 0.i % chitosan solution. However, the powder would not dissolve in the 2% acetic acid solution, demonstrating that the chitosan formed by this process was not of high purity.

These experiments demonstrate the advantages in making purified chitosan with an initial step of heating followed by immediate quenching at low temperature.

EXAMPLE 8

Differential Scanning Calorimetry

Differential scanning calorimetry data on cleaned crawfish shells indicated an endotherm around 78° C. Without wishing to be bound by this theory, it is believed that this endotherm corresponds to a transition from a crystalline chitin to an amorphous chitin. Thus the heating that immediately precedes the low-temperature quenching should be conducted at or above the endotherm. It is possible that the temperature of the endotherm could vary among different species of crustaceans, or seasonally even among different batches of shells from the same species. As used in the specification and Claims, the "endotherm" is the temperature at which the endotherm occurs for a particular batch of crustacean shells, as measured by differential scanning calorimetry. The shells are preferably maintained at a temperature at or above the endotherm for more than 24 hours, preferably about 48 hours.

EXAMPLE 9

Biocompatibility in Rats

Ten chitosan capsules, 1.0 mg each, were prepared from the purified chitosan. To prepare a capsule, 1.0 mg of chitosan was placed on a damp, round gelatin sheet having a 0.5 cm radius, about 1 mm thick. A second piece of damp gelatin of the same size was placed on top of the first, sandwiching the chitosan between the two sheets. The capsules were placed in individual sterilization bags and sterilized with ethylene oxide.

Three rats were anesthetized with pentabarbitol. A 2 cm dorsal incision was made in each rat directly behind the skull. Two chitosan capsules were placed in the subcutaneous tissue between the epithelium and the underlying superficial fascia, one capsule on the right lateral surface and the other on the left lateral surface. The incision was then closed using non-absorbable sutures. This procedure was performed on a total of three rats using six of the chitosan capsules.

One rat was sacrificed by carbon dioxide asphyxiation after 7 days, one rat after 14 days, and one after 21 days. After sacrificing each rat, the initial incision was reopened, and the skin was peeled back from the underlying muscle to reveal the site of the capsule implantation. The site of implantation of each capsule in each rat was observed for the presence or absence of inflammation, swelling, and infection.

After the visual observations were recorded, tissues from the implant sites were harvested. The harvested tissues were embedded in paraffin, sectioned, mounted on slides, and stained with Mason's Trichrome Stain. The stained slides were sent to a pathologist to examine for any evidence of rejection. Results are shown in Table 2.

TABLE 2

|  | Right Chitosan Capsule | Left Chitosan Capsule |
| --- | --- | --- |
| Rat 1 (7 Day Trial) | No Discernible Reaction | Slight Redness & Irritation |
| Rat 2 (14 Day Trial) | No Discernible Reaction | No Discernible Reaction |
| Rat 3 (21 Day Trial) | No Discernible Reaction | No Discernible Reaction |

These results demonstrate the biocompatibility of chitosan prepared with the new method. As used in the specification and claims, a chitosan is considered to be "biocompatible" if it does not induce an acute or chronic inflammatory response in mammalian tissue, and if it does not cause a significant change in mammalian tissue surrounding an implant formed from the chitosan.

The complete disclosures of all references cited in this specification are hereby incorporated by reference. In the event of an otherwise irreconcilable conflict, however, the present specification shall control.

I claim:

1. A process for preparing chitin-containing, cleaned crustacean shells for chitin production or for chitosan production, said process comprising the steps of:

(a) maintaining the shells at a temperature above about 78° C. for more than about 24 hours; and (b) cooling the shells by transferring the shells immediately from the maintained temperature into liquid nitrogen.

2. A process for preparing chitin-containing, cleaned crustacean shells for chitin production or for chitosan production, said process comprising the steps of:

(a) maintaining the shells at a temperature above about 78° C. for more than about 24 hours; and (b) cooling the shells by transferring the shells immediately from the maintained temperature into a liquid—dry ice bath.

3. A process for producing chitin, said process comprising the steps of:

(a) preparing crustacean shells by the process recited in claim 1;

(b) deproteinizing the prepared shells; and (c) demineralizing the prepared shells;

whereby chitin is produced.

4. A process as recited in claim 3, wherein said deproteinizing step comprises reacting the shells with aqueous sodium hydroxide and heat, and wherein said demineralizing step comprises reacting the shells with hydrochloric acid.

5. A process for producing chitosan, said process comprising the steps of:

(a) producing chitin by the process recited in claim 3; and (b) deacetylating the chitin;

whereby chitosan is produced.

6. A process as recited in claim 5, wherein said deproteinizing step comprises reacting the shells with aqueous sodium hydroxide and heat; wherein said demineralizing step comprises reacting the shells with hydrochloric acid; and wherein said deacetylating step comprises reacting the chitin with sodium hydroxide and heat.

7. A process as recited in claim 5, additionally comprising the step of purifying the chitosan by dialysis, so that the purified chitosan is biocompatible.

8. A process for producing chitin, said process comprising the steps of:

(a) preparing crustacean shells by the process recited in claim 2;

(b) deproteinizing the prepared shells; and (c) demineralizing the prepared shells;

whereby chitin is produced.

9. A process as recited in claim 8, wherein said deproteinizing step comprises reacting the shells with aqueous sodium hydroxide and heat; and wherein said demineralizing step comprises reacting the shells with hydrochloric acid.

10. A process for producing chitosan, said process comprising the steps of:

(a) producing chitin by the process recited in claim 8; and (b) deacetylating the chitin;

whereby chitosan is produced.

11. A process as recited in claim 10, wherein said deproteinizing step comprises reacting the shells with aqueous sodium hydroxide and heat; wherein said demineralizing step comprises reacting the shells with hydrochloric acid; and wherein said deacetylating step comprises reacting the chitin with sodium hydroxide and heat.

12. A process as recited in claim 10, additionally comprising the step of purifying the chitosan by dialysis, so that the purified chitosan is biocompatible.

* * * * *